(12) United States Patent
Abimosleh et al.

(10) Patent No.: US 8,641,780 B2
(45) Date of Patent: Feb. 4, 2014

(54) ADJUSTMENT DEVICE FOR A LOWER LIMB PROSTHESIS

(75) Inventors: Fadi Abimosleh, Springboro, OH (US); Graham Harris, Hampshire (GB); Stephen Terry Lang, Hampshire (GB); Mir Saeed Zahedi, London (GB)

(73) Assignee: Blatchford Products Limited, Hampshire (GB)

( * ) Notice: Subject to any disclaimer, the term of this patent is extended or adjusted under 35 U.S.C. 154(b) by 58 days.

(21) Appl. No.: 12/093,355

(22) PCT Filed: Nov. 14, 2006

(86) PCT No.: PCT/GB2006/004247
§ 371 (c)(1),
(2), (4) Date: May 12, 2008

(87) PCT Pub. No.: WO2007/054736
PCT Pub. Date: May 18, 2007

(65) Prior Publication Data
US 2008/0281435 A1    Nov. 13, 2008

Related U.S. Application Data

(60) Provisional application No. 60/736,409, filed on Nov. 14, 2005.

(51) Int. Cl.
*A61F 2/62* (2006.01)
*A61F 2/66* (2006.01)

(52) U.S. Cl.
USPC ............................................. 623/50; 623/53

(58) Field of Classification Search
USPC ............................. 623/26–27, 47–53, 55–56
See application file for complete search history.

(56) References Cited

U.S. PATENT DOCUMENTS

| 37,637 A | 2/1863 | Parmelee |
| 2,657,393 A | 11/1953 | Haller |

(Continued)

FOREIGN PATENT DOCUMENTS

| DE | 21 01 303 | 6/1972 |
| EP | 0 549 855 | 7/1993 |

(Continued)

OTHER PUBLICATIONS

Airline Hydraulic's, Hydraulic Schematic Symbols: Basic Symbols, website: http://www.airlinehyd.com/knowledgecenter/symbols.asp accessed May 15, 2010.*

(Continued)

*Primary Examiner* — Marcia Hoffman
(74) *Attorney, Agent, or Firm* — Alston & Bird LLP (57) ABSTRACT

An hydraulic heel-height adjustment device for a lower limb prosthesis has a foot-mounting component (18) for detachably mounting a prosthetic foot and a shin component pivotally connected to the foot-mounting component allowing angular adjustment of the foot-mounting component relative to the shin component about a heel-height adjustment axis. The relative angular position is set by an hydraulic piston (42) and cylinder assembly which has a chamber (40) in the shin component containing a piston (42) arranged to execute a translational movement in the chamber when adjustment is required. A bypass passage interconnects parts of the chamber on opposite sides of the piston, this passage containing a manually operable valve which is spring-biased towards a closed position. The piston has a piston rod pivotally connected to the foot-mounting component by a pivot joint defining a medial-lateral axis parallel to and spaced from the heel-height adjustment axis.

30 Claims, 4 Drawing Sheets

(56) References Cited

U.S. PATENT DOCUMENTS

| | | | |
|---|---|---|---|
| 3,871,032 A | 3/1975 | Karas | |
| 4,051,558 A | 10/1977 | Vallotton | |
| 5,957,981 A * | 9/1999 | Gramnas | 623/47 |
| 6,033,440 A * | 3/2000 | Schall et al. | 623/38 |
| 6,187,052 B1 * | 2/2001 | Molino et al. | 623/52 |
| 6,443,993 B1 * | 9/2002 | Koniuk | 623/24 |
| 6,863,695 B2 * | 3/2005 | Doddroe et al. | 623/55 |
| 7,052,519 B1 * | 5/2006 | Gramnas | 623/52 |
| 7,318,504 B2 * | 1/2008 | Vitale et al. | 188/265 |
| 2002/0052663 A1 | 5/2002 | Herr et al. | |
| 2002/0138153 A1 | 9/2002 | Koniuk | |
| 2004/0044417 A1 | 3/2004 | Gramnas | |
| 2004/0236435 A1 | 11/2004 | Chen | |
| 2006/0235544 A1 | 10/2006 | Iversen et al. | |
| 2006/0249315 A1 | 11/2006 | Herr et al. | |

FOREIGN PATENT DOCUMENTS

| | | |
|---|---|---|
| EP | 0 948 947 | 10/1999 |
| EP | 1 068 844 | 1/2001 |
| GB | 643734 | 9/1950 |
| GB | 2 328 160 | 2/1999 |
| JP | 59 183747 | 10/1984 |
| JP | 59 189843 | 10/1984 |
| WO | WO 96/25898 | 8/1996 |
| WO | WO 99/00075 | 1/1999 |
| WO | WO 00/76429 | 12/2000 |
| WO | WO 02/15826 | 2/2002 |
| WO | WO 03/086245 | 10/2003 |
| WO | WO 2006/112774 | 10/2006 |
| WO | WO 2007/027808 | 3/2007 |

OTHER PUBLICATIONS

The International Search Report for PCT Application No. PCT/GB2006/004247; Filed Nov. 14, 2006; Date of Completion May 31, 2007; Date of Mailing Jun. 6, 2007.

The Written Opinion for PCT Application No. PCT/GB2006/004247; Filed Nov. 14, 2006; Date of Completion May 31, 2007; Date of Mailing Jun. 6, 2007.

*Hydraulic Ankle Unit Manual*; Mauck Laboratories, Inc.; First Printing Mar. 1988.

* cited by examiner

ADJUSTMENT DEVICE FOR A LOWER LIMB PROSTHESIS

CROSS REFERENCE TO RELATED APPLICATIONS

This application is a national phase entry of International Application No. PCT/GB06/04247, filed Nov. 14, 2006, which claims priority to U.S. Provisional Application No. 60/736,409, filed Nov. 14, 2005, the entire contents of which are incorporated herein by reference.

BACKGROUND OF THE INVENTION

This invention relates to an adjustment device and a lower limb prosthesis including such a device. The invention is of particular relevance to heel-height adjustment.

A known adjustable prosthetic joint for setting the angular position of a prosthetic foot with respect to a prosthetic shin component is disclosed in U.S. Pat. No. 5,957,981 (Gramnäs). This known joint comprises a pair of vane pistons located in fluid-containing chambers which are interconnected by a bypass valve allowing or preventing the passage of fluid between the chambers according to the setting of the valve. The assembly of the pistons, the chamber walls, and the rotary interconnection of the pistons and the chamber walls forms part of a prosthetic foot with a proximal clamp for receiving a shin tube. The valve is manually operable using a rotatable lever on the side of the assembly, allowing the prosthesis wearer to open the valve when angular adjustment is required.

A disadvantage of the known arrangement is that the assembly is bulky, particularly in the anterior-posterior direction. This and the incorporation of the assembly in the foot tends to restrict the choice of foot configuration available for the wearer.

A joint allowing dynamic hydraulic control of the angular position of a prosthetic foot with respect to a shin component is disclosed in Mauch Laboratories, Inc., Hydraulik Ankle Unit Manual, page 2, March 1998. This suffers from similar disadvantages.

SUMMARY OF THE INVENTION

It is an object of the invention to provide an improved means of allowing adjustment of the relative angular position of a prosthetic foot with respect to a prosthetic shin component.

According to a first aspect of this invention there is provided an hydraulic heel-height adjustment device for a lower limb prosthesis, comprising: a foot-mounting component for detachably mounting a prosthetic foot and a shin component pivotally connected to the foot-mounting component, wherein the shin component has a chamber containing a piston arranged to execute a translational movement in the chamber with the volume of part of the chamber varying as the piston moves, and a passage which communicates with the chamber part and contains a valve for controlling the flow of fluid in the passage and thereby the movement of the piston, the piston being connected to the foot-mounting component such that when the valve is open the relative angular position of the foot-mounting and shin components can be adjusted, and when the valve is closed the said relative angular position is locked. The chamber preferably contains an hydraulic fluid and is advantageously cylindrical, its central axis being longitudinally oriented so as to be coincident with or parallel to a shin axis defined by the shin component, and the diameter of the chamber being at least 25 mm. Use of a single cylinder substantially centred on the shin axis allows a large piston area to be accommodated within an ankle component of a diameter not much greater than that of the shin tube. In some embodiments, the shin component is a shin tube section and the chamber is housed within the shin tube section. The piston preferably has a piston rod which is pivotally coupled to the foot-mounting component, the piston rod passing in a sealed fluid-tight manner through at least one of upper and lower internal transverse walls bounding the chamber inside the shin component.

The pivotal interconnection of the foot-mounting and shin components typically defines a medial-lateral heel-height adjustment axis offset anteriorly from the shin axis, the piston rod being coupled to the foot-mounting component by a pivot joint defining a pivot axis which is parallel to and spaced posteriorly with respect to the heel-height adjustment axis. In the context of the present invention, the term "medial-lateral heel-height adjustment axis" means an axis, which itself extends in a medial-lateral direction, and about which the foot-mounting component or foot pivots in a dorsi-plantar rotational sense relative to the shin component or shin member to adjust heel-height.

Preferably, the pivot joint defines a single pivot axis with the piston rod being directly pivotally connected to the foot-mounting component. The cylinder, the piston and the piston rod may be dimensioned to allow the piston and piston rod to float in the cylinder to allow misalignment between the central axis of the piston and piston rod and the central axis of the cylinder as the angle between the foot-mounting and shin components is adjusted.

Alternatively, the piston rod is coupled indirectly to the foot-mounting component by a connecting link pivotally mounted on the foot-mounting component so as to be pivotable relative thereto about an axis which is parallel and spaced anteriorly with respect to the heel-height adjustment axis.

The heel-height adjustment axis may be offset posteriorly rather than anteriorly from the shin axis.

In this way, by providing a piston which executes translational movement inside a component associated with the shin to control the angular position of a foot-mounting component located distally of the shin, the device can be located proximally of a foot connection interface without occupying excessive space. This allows the attachment of a range of different prosthetic feet by the wearer or prosthetist. In addition, prosthetic feet may be interchanged without incurring the cost of replacing the heel-height adjustment device.

The foot-mounting component preferably includes a pyramid connection socket for receiving a conventional male four-sided inverted-pyramid connection of a prosthetic foot, allowing a good selection of different prosthetic feet to be interfaced with the device. The pyramid connection interface typically includes alignment means allowing at least inversion-eversion alignment.

Prosthetic feet to be attached to the foot-mounting component of the preferred device include feet the height of which, measured from the sole to the highest weight-bearing surface portion of the foot which engages the connector is at least 70 mm. This is equivalent, typically, to a ground to mounting-interface height of 80 mm.

The valve may be wearer-operable and may have an operating button projecting from one side of the device, preferably the lateral side. The valve member is preferably spring-loaded towards its closed position.

According to a second aspect of the invention, there is provided a lower limb prosthesis comprising a stump socket, a shin member connected to the stump socket, and a foot-mounting connector on the distal end of the shin member, wherein the shin member includes an hydraulic heel-height adjustment device for pivoting the foot-mounting connector about a medial-lateral heel-height adjustment axis, the device including a piston that is movable within a chamber located inside the shin member and that has a piston rod connected to the foot-mounting connector by a pivot joint defining a pivot axis parallel to the heel-height adjustment axis, at least a part of the chamber varying in volume as the piston moves, and a valve for controlling the flow of fluid in a passage communicating with the chamber, the valve and piston being operable to set the angular position of the foot-mounting connection about the said axis.

According to a third aspect of the invention there is provided a lower limb prosthesis comprising a stump socket, a shin member, a knee joint interconnecting the shin member and the stump socket, and a foot-mounting connector on the distal end of the shin member, wherein the shin member includes an hydraulic heel-height adjustment device including a piston movable within a fluid-filled chamber located inside the shin member for pivoting the foot-mounting connector about a medial-lateral heel-height adjustment axis.

According to a fourth aspect of the invention, there is provided a lower limb prosthesis comprising a stump socket, a prosthetic shin member connected to the stump socket, and a prosthetic foot member connected to the shin member by an hydraulic mechanism arranged to alter the relative angular position of the foot member and the shin member about a medial-lateral adjustment axis, wherein the mechanism comprises a first pivotal connection of the foot member to the shin member defining the said adjustment axis, and a piston and cylinder assembly interconnecting the foot and shin members and offset to one side of the adjustment axis, wherein the piston and cylinder assembly has a piston component translationally moveable in a cylinder component, one of which components is rigidly connected to one of the foot member and the shin member and the other of which components is pivotally attached to the other of the foot member and the shin member, and wherein the piston and cylinder assembly is constructed to allow the piston component to move other than axially within the cylinder component.

The cylinder component is preferably associated with the shin member and the piston component has a piston rod preferably pivotally connected to the foot member by a pivot joint defining a single pivot axis parallel to the adjustment axis.

BRIEF DESCRIPTION OF THE DRAWINGS

The invention will now be described by way of example with reference to the drawings in which.

DETAILED DESCRIPTION OF THE DRAWINGS

Figure 1A:
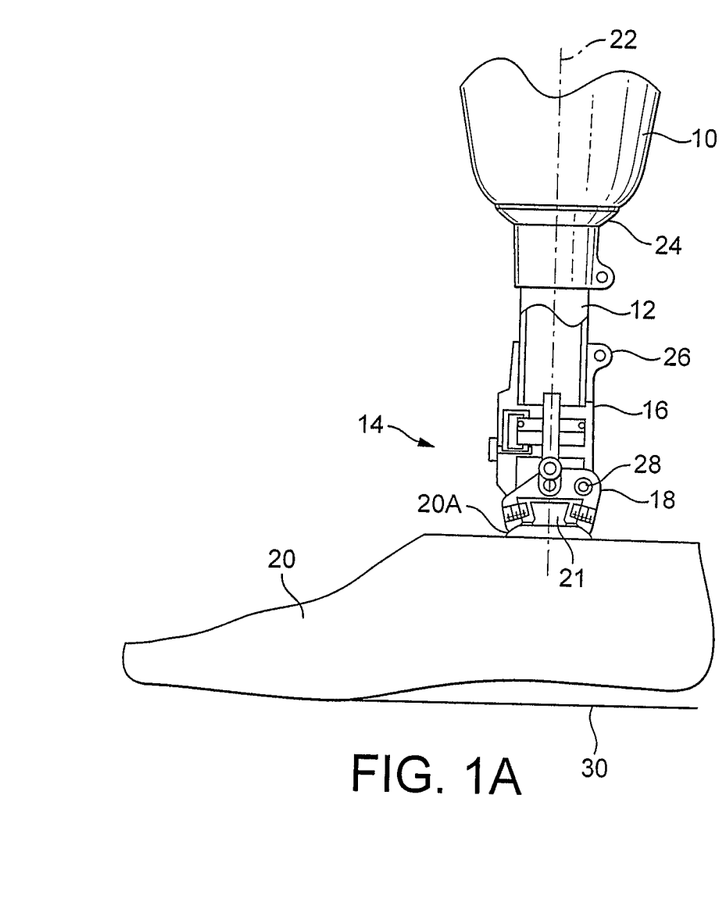
FIGS. 1A and 1B are diagrammatic side views of a lower limb prosthesis incorporating a heel-height adjustment device in accordance with the present invention, showing the device set for different heel heights.
Figure 1B:
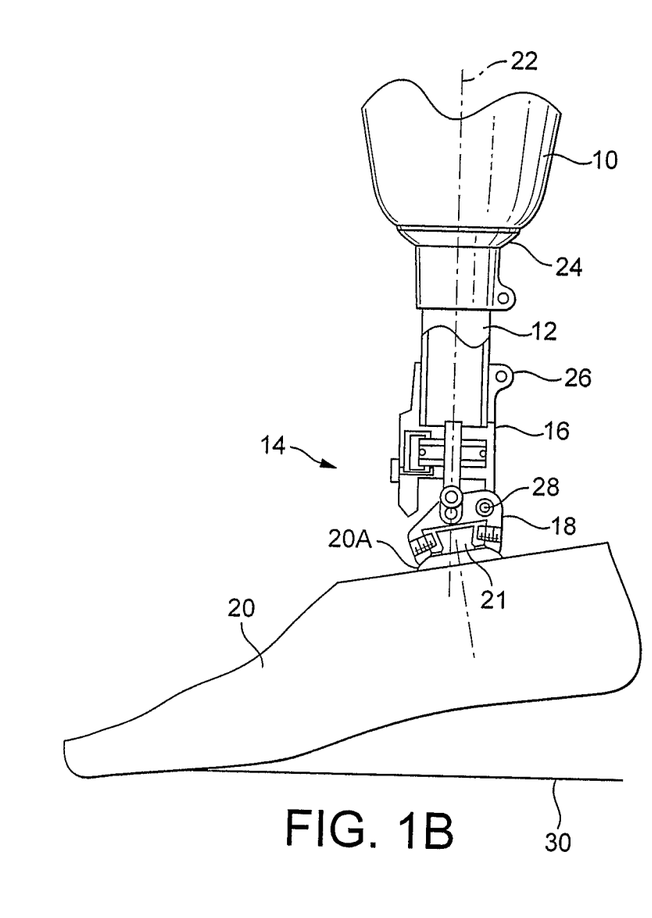

Referring to FIGS. 1A and 1B, a prosthesis for a below-knee amputee comprises a stump socket 10 (only part of which is shown), a shin tube 12, shown partly in cross section, an hydraulic heel-height adjustment device 14 having a shin component 16 and a foot-mounting component 18, and, mounted to the foot-mounting component 18, a prosthetic foot 20.

The shin tube 12 defines a shin axis 22 and has a proximal end portion clamped to the socket 10 by an upper alignment component 24 and a distal end portion secured in a shin tube clamp 26 of the shin component 16.

The shin component 16 and the foot-mounting component 18 of the heel-height adjustment device 14 are pivotable relative to each other about a heel-height adjustment axis 28 running in the medial-lateral direction so that when the foot-mounting component 18 is pivoted in the plantar direction relative to the shin component 16, the heel-height of the foot 20 relative to the ground 30 is increased, as shown in FIG. 1B.

Figure 2A:
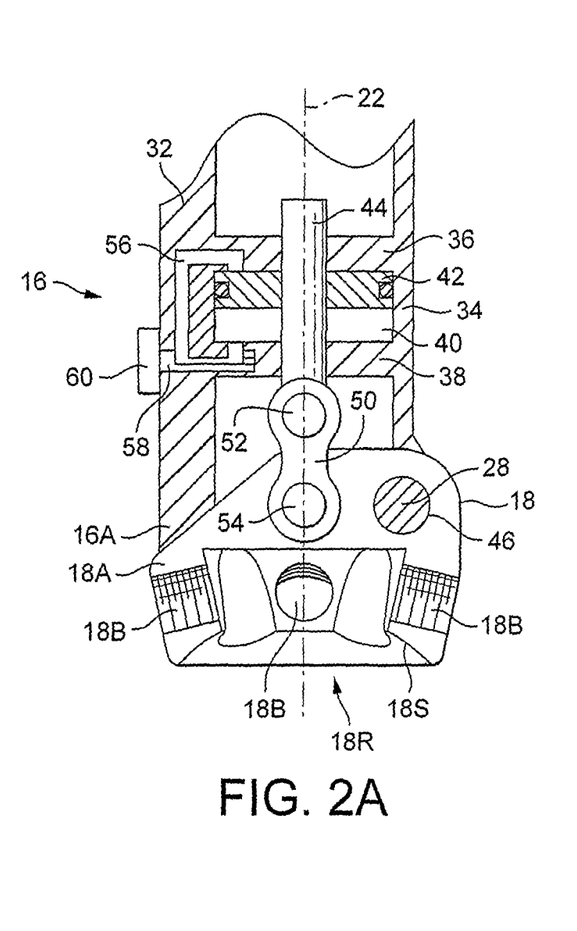
FIGS. 2A and 2B are diagrammatic cross sections of the heel-height adjustment device used in the prosthesis of FIGS. 1A and 1B, shown in two states, corresponding to different heel-height settings.
Figure 2B:
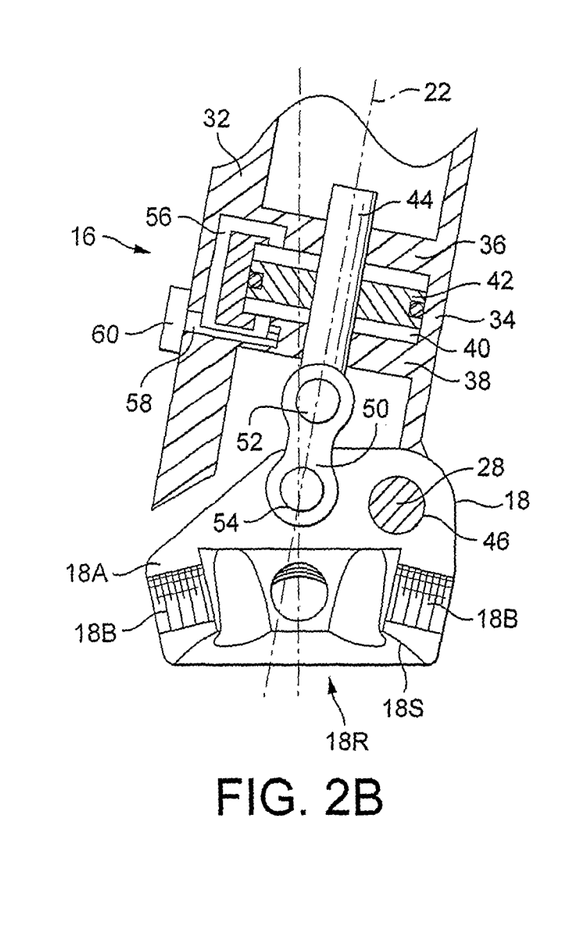

The heel-height adjustment device is shown in more detail in FIGS. 2A and 2B. The shin component 16 of the heel-height adjustment device 14 is generally tubular and forms a shin tube section. The shin tube section is centred on the shin axis 22 and has a cylindrical tubular side wall 34, and two spaced-apart transverse walls 36, 38 which are perpendicular to the shin axis 22 and define between them a cylindrical chamber 40, the axis of which is directed longitudinally of the shin axis. The diameter of the chamber is greater than 25 mm and, in the preferred embodiment of the invention, between 30 mm and 35 mm. In the preferred embodiment, the cylindrical chamber is coaxial with the shin.

Linearly movable inside the chamber 40 is a piston 42 having a piston rod 44 which extends through bores in each of the transverse plates 36, 38. In this embodiment of the invention, the piston and the cylinder formed by the tubular and transverse walls 34, 36, 38 of the shin component 16 are centred on the shin axis 22.

The heel-height adjustment axis 28 is defined by a pivot pin 46 forming part of the shin component 16 and housed in a bore in the foot-mounting component 18. It will be noted that, in this embodiment, the heel-height adjustment axis 28 is on the posterior side of the shin axis 22, and spaced from the latter by a distance approximately equal to the radius of a shin tube clamped in the shin component 16.

The foot-mounting component 18 is configured as a pyramid connection socket for receiving a four-sided male inverted-pyramid connection 21 (see FIGS. 1A and 1B) of the prosthetic foot 20. Four threaded bores 18B are provided in the conventional manner for screws (not shown in FIGS. 2A and 2B) for inversion-eversion and plantar-dorsi alignment of the foot 20 relative to the foot-mounting component 18. The interface provided by the pyramid connection socket therefore takes the form of a distally directed receptacle 18R which is bounded by an annular part-spherical distally-directed abutment surface 18S for abutting a corresponding part-spherical distally directed abutment surface 20A on the foot 20 (FIG. 1A). Abutment surface 20A extends annularly around the inverted pyramid connection 21.

The angular position of the foot-mounting component 18 is determined by the translational position of the piston 42 in the shin component 16 since the distal end of the piston rod 44 is pivotally connected to the foot-mounting component 18. In this embodiment, the connection is performed by a link member 50 having proximal and distal pivot connections 52, 54 with the piston rod 44 and the foot-mounting component 18 respectively, the pivot axis defined by the distal pivotal connection being spaced anteriorly in the foot-mounting component 18 from the heel-height adjustment axis 28. Accordingly, when the piston 42 moves distally in the chamber 40 from its uppermost position as shown in a FIG. 2A to a lower position as shown in FIG. 2B, the foot-mounting component 18 pivots in the plantar direction, thereby increasing the heel-height of the foot 20 as shown in FIG. 1B. In a minimum heel-height configuration, an anterior portion 18A of the foot-mounting component 18 abuts an anterior stop 16A on the shin component 16 as shown in FIG. 1A.

The chamber 40 is filled with hydraulic fluid on both sides of the piston 42. Movement of the piston 42 is controlled by controlling the flow of fluid in a bypass passage 56 extending through the body of the shin component 16 between the chamber parts on opposite sides of the piston 42. A spool valve 58, shown diagrammatically in FIGS. 2A and 2B, is used to prevent or allow the flow of fluid and, hence, movement of the piston, as will be described in more detail below. The spool valve 58 is operated manually by a control 60 on the outside of the shin component tubular wall 32. When the valve 58 is closed, the position of the piston 42 is fixed, thereby fixing the heel-height. When the valve 58 is open, the wearer of the prosthesis can alter the heel-height by, e.g. placing the foot on a firm surface and moving the shin anteriorly or posteriorly as required to move the piston 42 in the chamber 40 thereby to decrease or increase heel-height, e.g. to suit a different shoe. Typically, the wearer performs the adjustment whilst wearing the shoe and moves the shin to bring the shin axis 22 vertical. The button 60 is then released to close the valve 58, whereafter the heel-height for that particular shoe is maintained.

Figures 3A, 3B, 3C, 3D, 3E:
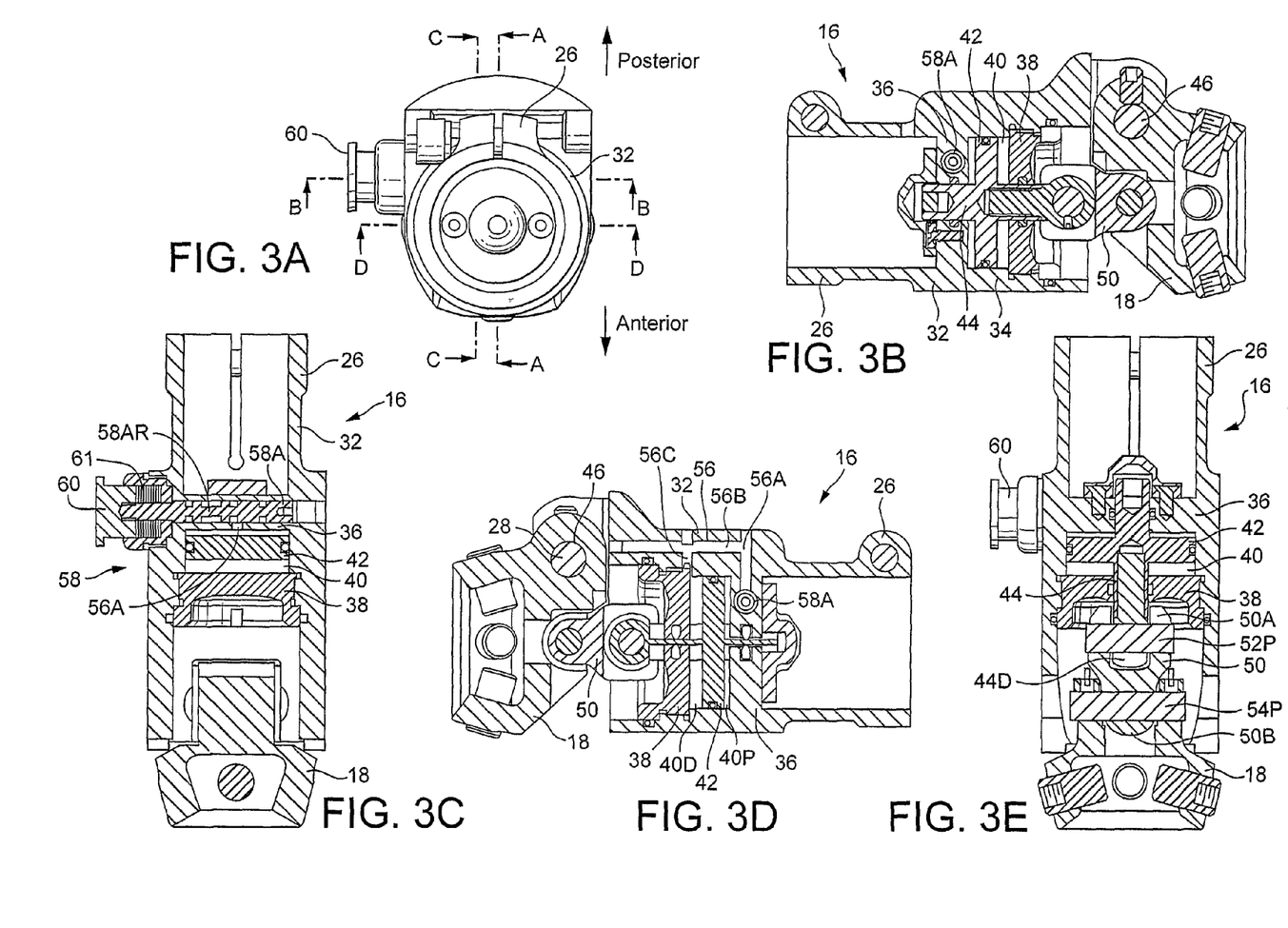
FIGS. 3A to 3E show a heel-height adjustment device in accordance with the invention, being respectively a plan view, a cross-section on the central anterior-posterior plane A-A shown in FIG. 3A, a cross-section on the posteriorly offset medial-lateral plane B-B shown in FIG. 3A, a cross-section on the laterally offset anterior-posterior plane C-C shown in FIG. 3A, and a cross-section on the central medial-lateral plane D-D shown in FIG. 3A.

FIGS. 3A to 3D are views of another embodiment of the invention. Referring to FIGS. 3C and 3D, it will be seen that, in this embodiment, the valve 58 is a spool valve having a spool member 58A extending in the medial-lateral direction through the upper transverse wall 36. The bypass passage 56 between proximal and distal parts 40P, 40D of the chamber 40 on opposite sides of the piston 42 has an upper section 56A in the upper transverse wall 36, an intermediate section 56B in the tubular side wall 32, and a lower section 56C opening into the distal chamber portion 40D. Referring to FIG. 3C, it will be seen that the spool member 58A has a reduced diameter portion 58AR which may be brought into registry with the upper section 56A of the bypass passage 56 by pushing the control button 60, thereby opening the valve 58 and allowing the flow of fluid from one side of the piston 42 to the other via the bypass passage 56.

A compression spring 61 biases the spool member 58A towards the closed position.

As shown in FIGS. 3B to 3E, the diameter of the cylinder formed by the tubular wall 32 and, therefore, the diameter of the piston 42, is substantially equal to the internal diameter of the shin tube clamp 26. Having a piston diameter of this order means that the medial-lateral and anterior-posterior dimensions of the shin component 16 of the device need not be excessively greater than the diameter of the shin tube clamp, yielding the benefit that much of the mechanism of the device can be accommodated in the lower part of the shin portion of the prosthesis rather than in the foot. It is possible, indeed, to construct the shin component 16 as part of a single tubular shin portion of the prosthesis rather than as a shin tube section which is clamped to a shin tube. In addition, the diameter of the piston can be reduced compared with the piston 42 of this preferred embodiment to make the external dimensions of the device at the shin level even smaller. Thus, the diameter of the piston 42 and its chamber may be less than the internal diameter of a shin tube.

Referring to FIG. 3E, in this embodiment, the link 50 has an upper yoke portion 50A which receives a distal portion 44D of the piston rod 44 and is connected to the latter by an upper pivot pin 52P. The lower part 50B of the link 50 carries a lower pivot pin 54P housed in the foot-mounting component 18.

Figure 4:
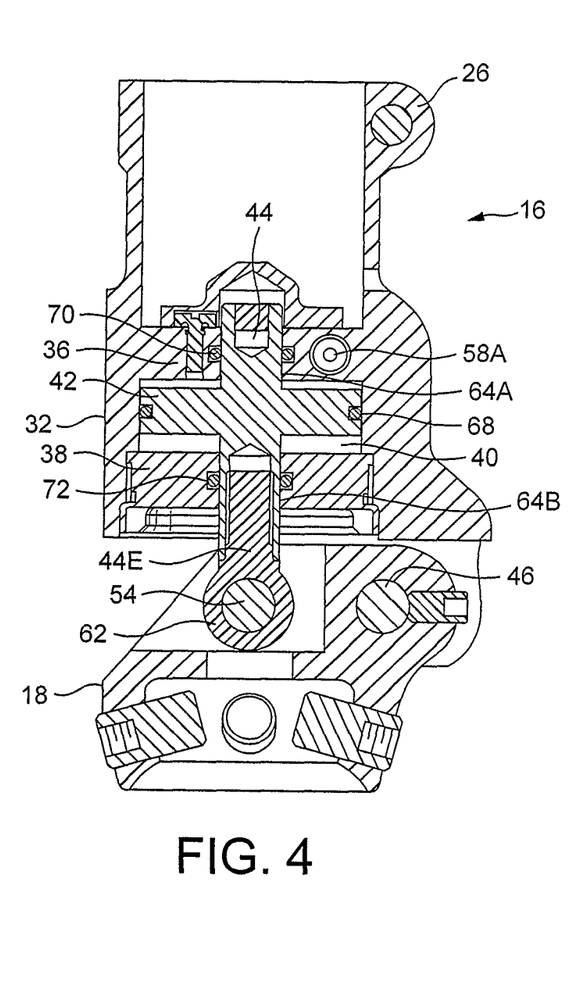
FIG. 4 is a cross section of an alternative heel-height adjustment device in accordance with the invention, being a cross-section on the central anterior-posterior plane.

Referring to FIG. 4, in an alternative embodiment, the link 50 of the embodiment described above is replaced by an extension 44E of the piston rod 44. This piston rod extension includes a bush 62 housing the medial-lateral pivot pin 54 which is rotatable in the foot-mounting component 18. In this way, therefore, the piston rod 44 is connected directly to the foot-mounting component 18 by a single pivotal connection. A particular feature of this embodiment is that the pivot pin 54 has a central section which is eccentrically offset from the end portions of the pin (the latter being housed in the foot-mounting component 18), the pin 54 being rotatable in both the foot-mounting component 18 and the bush 62 of the piston rod extension 44E to allow for movement of the pivot axis defined by the mounting of the pivot pin 54 in the foot-mounting component 18. It will be understood that this pivot axis moves away from the axis of the piston rod 44 as the foot-mounting component 18 rotates about the heel-height adjustment axis 28 in the plantar direction.

In this embodiment, heel-height adjustment limits are defined by abutment of the piston 42 against the transverse walls 36, 38.

Figure 5:
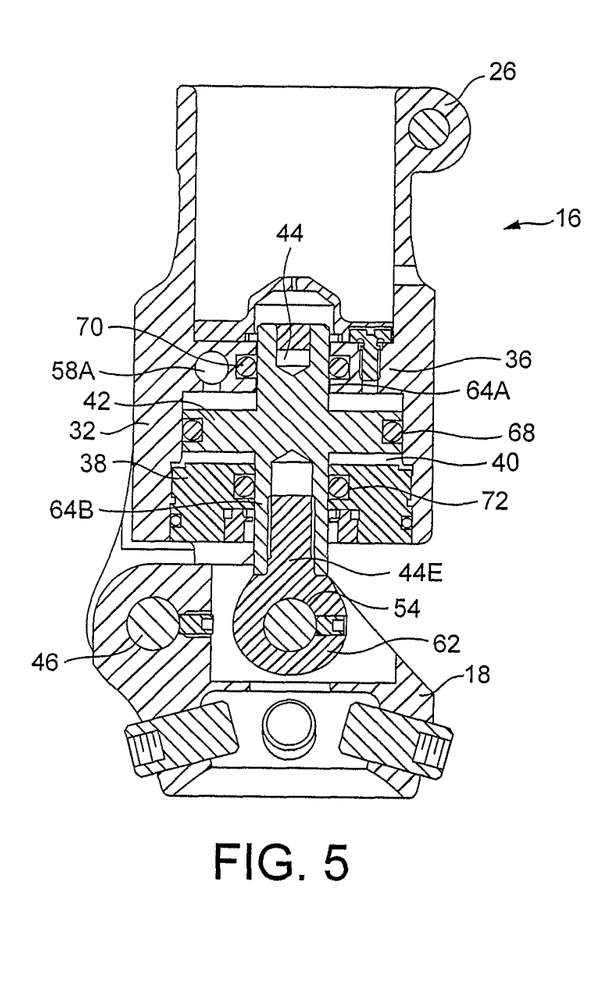
FIG. 5 is a cross section of yet a further alternative heel-height adjustment device in accordance with the invention, also being a cross section on a central anterior-posterior plane.

The eccentric rotating pivot pin connection described above is preferably dispensed with in a particularly preferred embodiment, shown in FIG. 5, in which the piston rod 44 is connected directly to the foot-mounting component 18 by a simple pin fixed in the bush 62, as shown, or in the foot-mounting component 18. The pivot pin 54, therefore, defines a single pivot axis. The resultant potential misalignment between the central axis of piston 42 and the piston rod 44 on the one hand and the axis of the cylinder 32 and the bores housing the piston rod 44 in the transverse walls 36, 38 on the other hand is accommodated by allowing for the piston 42 and the piston rod 44 to rock by a small degree in the chamber 40 and the piston rod bores 64A, 64B in the transverse walls 36, 38. In this modification, the clearances between the piston rod 44 and the bores 64, 66 are increased compared with the previously-described embodiments to allow for a small degree of angular deviation of the piston rod 44 and piston 42 from the axis of the cylindrical chamber 40. In this embodiment, the radial clearance around the piston rod 44 in the bores 64, 66 is about 0.13 mm. In addition, the periphery of the piston 42 is barrel-shaped to maintain its clearance from the cylinder wall as the piston rocks. A further measure to accommodate misalignment consists of offsetting the axis of the pivot pin 54 (and hence the axis of the piston rod 44 at its connection to the foot-mounting component 18) with respect to the shin axis in a direction away from the heel-height adjustment axis. This offset occurs when the foot-mounting component 18 is in a neutral or mid position with respect to the shin component 16. In this embodiment the offset at the neutral position is about 0.1 mm. Elastomeric sealing members 68, 70, 72, here in the form of rubber O-rings, and the grooves in which they are seated, are dimensioned to maintain the respective fluid-tight seals. Another feature of this preferred embodiment is that the heel-height adjustment axis is located anteriorly with respect to the shin axis and the pivot axis of the pivot joint connecting the pivot rod 44 to the foot-mounting component 18. In other respects, the device of FIG. 5 is similar to those illustrated in FIGS. 3A to 3E and FIG. 4.

In summary, by forming the heel-height adjustment device as a converter for converting substantially linear movement of a control part in an upper portion of the device to rotary (pivotal) movement of a lower part of the device, the device can be made sufficiently slim that it can form part of a prosthetic shin, thereby allowing a foot-mounting interface beneath the heel-height adjustment axis. The device may include a shin tube clamp as in the described and illustrated embodiments, or it may form part of an integral shin member. In either case, the shin tube or shin member can be cut to a required length according to the vertical extent of a selected prosthetic foot. In this way, prosthetic feet of different vertical dimensions may be accommodated, including feet having a ground-to-connection vertical distance in excess of 80 mm. In practice, this means that, with a heel-height of 10 mm (a typical minimum heel-height), prosthetic feet in which the distance between the sole and, e.g. the uppermost abutment surface of the connection interface, can be greater than 70 mm if necessary. In the case of the connection interface being a conventional pyramid connection as described and shown above, the vertical measurements referred to above are made with respect to the uppermost part of the annular abutment surface extending around the male inverted-pyramid connection on the prosthetic foot. The measurement is made from this surface part to a portion of the sole vertically beneath the interface, i.e. on the pyramid axis.

Use of an hydraulic piston and cylinder arrangement, combined with a valved bypass passage allows a smooth, stepless adjustment with an infinite number of heel-height positions.

The invention claimed is:

1. A lower limb prosthesis comprising a stump socket, a shin member connected to the stump socket, and a foot-mounting connector directly pivotally connected to a distal end of the shin member at a medial-lateral heel-height adjustment axis so as to pivot relative to the shin member about the medial-lateral heel-height adjustment axis, wherein the shin member defines a shin axis which extends substantially vertically when an amputee is standing on flat ground and which is spaced-apart from the heel-height adjustment axis, the shin member including a hydraulic heel-height adjustment device including a linear piston and cylinder assembly comprising a piston movable substantially longitudinally of the shin member within a chamber located inside the shin member for pivoting the foot-mounting connector about said heel-height adjustment axis, at least a part of the chamber varying in volume as the piston moves, and wherein the piston has a piston rod connected to the foot-mounting connector by a pivot joint defining a pivot axis spaced-apart from and parallel to the heel-height adjustment axis.

2. A prosthesis according to claim 1, wherein the chamber is cylindrical and has a central axis oriented substantially longitudinally of the shin member.

3. A prosthesis according to claim 2, wherein the shin member is a shin tube defining said shin axis which is substantially coincident with the central axis of the chamber, and the piston diameter is smaller than or equal to an internal diameter of the shin tube.

4. A prosthesis according to claim 2, wherein the piston rod is directly pivotally coupled to the foot-mounting connector by a pivot joint defining a single axis parallel to the heel-height adjustment axis.

5. A prosthesis according to claim 4, configured such that the piston and the piston rod are allowed to move other than axially within the chamber.

6. A lower limb prosthesis comprising a stump socket, a shin member connected to the stump socket, and a foot-mounting connector directly pivotally connected to the distal end of the shin member at a medial-lateral heel-height adjustment axis so as to pivot relative to the shin member about the medial-lateral heel-height adjustment axis, wherein the shin member includes a hydraulic heel-height adjustment device for pivoting the foot-mounting connector about said heel-height adjustment axis, the device including a linear piston and cylinder assembly comprising a piston that is movable within a chamber located inside the shin member and that has a piston rod connected to the foot-mounting connector by a pivot joint defining a pivot axis parallel to and spaced from the heel-height adjustment axis, at least a part of the chamber varying in volume as the piston moves, and a valve for controlling the flow of fluid in a passage communicating with the said chamber part, the valve and piston being operable to set an angular position of the foot-mounting connector about the heel-height adjustment axis, wherein the shin member has a portion that extends proximally of the piston and cylinder assembly thereby to define a shin axis which extends substantially vertically when an amputee is standing on flat ground and which is spaced from the heel-height adjustment axis, and wherein the piston and cylinder assembly are oriented such that the piston executes said movement substantially axially with respect to said shin axis.

7. A prosthesis according to claim 6, wherein the foot-mounting connector includes an alignment interface for allowing at least alignment by inversion or eversion of a prosthetic foot mounted to the said connector.

8. A prosthesis according to claim 6, further comprising a prosthetic foot attached to the foot-mounting connector, the height of the foot measured from the sole to the highest weight-bearing surface portion of the foot which engages the connector being at least 70 mm.

9. A prosthesis according to claim 6, wherein the foot has a male inverted-pyramid connection portion received in the foot-mounting connector, and wherein the height of the foot measured from the sole to a proximally directed surface portion abutting the foot-mounting connector immediately adjacent the inverted pyramid is at least 70 mm.

10. A hydraulic heel-height adjustment device for a lower limb prosthesis, comprising:
   a foot-mounting component for detachably mounting a prosthetic foot and
   a shin component directly pivotally connected to the foot-mounting component at a medial-lateral heel-height adjustment axis so as to be pivotable relative to each other about a the medial-lateral heel-height adjustment axis,
   wherein the shin component has a chamber containing a piston arranged to execute a translational movement in the chamber with a volume of part of the chamber varying as the piston moves, and a passage which communicates with said chamber part and contains a valve for controlling the flow of fluid in the passage and thereby the movement of the piston, the foot-mounting component and the piston being connected at the foot-mounting component about a medial-lateral pivotal connection axis which is spaced-apart from the heel-height adjustment axis such that when the valve is open the piston can move in the chamber and a relative angular position of the foot-mounting and shin components can be adjusted and when the valve is closed the piston is locked in the chamber and the relative angular position is locked, and wherein the medial-lateral heel-height adjustment axis is spaced from a longitudinal shin axis which extends substantially vertically when an amputee is standing on flat ground and which is defined by the shin component.

11. A hydraulic heel-height adjustment device for a lower limb prosthesis, comprising:
a foot-mounting component for detachably mounting a prosthetic foot and
a shin component pivotally connected to the foot-mounting component and defining a shin axis extending in a direction longitudinally of the shin component,
wherein the shin component has a cylindrical chamber having a central axis and containing a piston arranged to execute a translational movement in the chamber with a volume of a part of the chamber varying as the piston moves, and a passage which communicates with said part of the chamber and contains a valve for controlling a flow of fluid in the passage and thereby the movement of the piston, wherein the shin component has a portion that extends proximally of the cylindrical chamber and the piston in said direction of said shin axis,
the chamber being oriented in the shin component with the central axis oriented in said direction of said shin axis, and wherein the piston is connected to the foot-mounting component such that when the valve is open the piston can move in the chamber and a relative angular position of the foot-mounting and shin components can be adjusted and when the valve is closed the piston is locked in the chamber and said relative angular position is locked, the valve being configured to be maintained closed throughout a gait cycle so as to fix the relative angular position at a required heel-height setting.

12. A device according to claim 11, wherein the shin component is a tube section defining said shin axis extending in a superior-inferior direction and wherein said central axis of the chamber is substantially coincident with the shin axis, and the piston has a piston rod which is pivotally coupled to the foot-mounting component.

13. A device according to claim 12, wherein the pivotal interconnection of the foot-mounting and shin tube components defines a medial-lateral heel-height adjustment axis which is anteriorly offset from the shin axis and the piston rod is secured to the foot-mounting component by a link having spaced-apart parallel medial-lateral pivotal connection axes.

14. A device according to claim 12, wherein the chamber is bounded by at least one transverse wall and wherein the device has a preset heel-height position defined by abutment of the piston against the wall.

15. A device according to claim 12, wherein the pivotal interconnection of the foot-mounting component and the shin component defines a heel-height adjustment axis which is spaced from the shin axis by a distance at least approximately equal to a tube radius of the shin tube section.

16. A device according to claim 12, wherein the chamber is defined by first and second spaced-apart internal transverse walls inside the shin component, the transverse walls extending substantially perpendicularly to the shin axis, and wherein the piston rod passes in a fluid-tight manner through at least one of the transverse walls.

17. A device according to claim 11, wherein the pivotal interconnection of the foot-mounting and shin components defines a medial-lateral heel-height adjustment axis, and the piston has a piston rod directly pivotally coupled to the foot-mounting component by a pivot joint defining a single pivot axis parallel to and spaced from the heel-height adjustment axis.

18. A device according to claim 17, configured such that the piston and the piston rod are allowed to move other than axially within the chamber.

19. A device according to claim 17, having a preset heel-height position defined by abutment of the shin tube component on the foot-mounting component at a location spaced from the heel-height adjustment axis in the anterior/posterior direction.

20. A device according to claim 11, wherein the pivotal interconnection of the foot-mounting and shin components defines a medial-lateral heel-height adjustment axis, and the piston has a piston rod coupled to the foot-mounting component by a connecting link pivotally mounted on the foot-mounting component so as to be pivotable relative thereto about an axis which is parallel to and spaced from the heel-height adjustment axis.

21. A device according to claim 11, wherein the passage is formed in a body of the shin component.

22. A device according to claim 21, wherein the valve includes a manually operable valve member projecting from the body of the shin component.

23. A device according to claim 11, wherein the foot-mounting component includes foot-shin alignment means.

24. A device according to claim 11, wherein the foot-mounting component includes a pyramid connection socket for receiving a four-sided male inverted-pyramid connection of said prosthetic foot.

25. A device according to claim 24, wherein the pivotal interconnection of the foot-mounting and shin components defines a medial-lateral heel-height adjustment axis which is at least 85 mm above ground level.

26. A device according to claim 11, wherein the foot-mounting component comprises an annular foot-mounting clamp having a central axis substantially coincident with the shin axis.

27. A lower limb prosthesis comprising a stump socket, a prosthetic shin member connected to the stump socket, and a prosthetic foot member connected to the shin member by a hydraulic mechanism arranged to alter a relative angular position of the foot member and the shin member about a medial-lateral adjustment axis, wherein the mechanism comprises a first direct pivotal connection of the foot member to the shin member defining the said adjustment axis, and a linear piston and cylinder assembly interconnecting the foot and shin members, the piston and cylinder assembly having a piston component translationally moveable in a cylinder component, the cylinder component having a central axis which extends substantially vertically when an amputee is standing on flat ground and which is spaced from the adjustment axis, one of said piston component and said cylinder component being rigidly connected to one of the foot member and the shin member and the other of said piston component and said cylinder component being pivotally attached to the other of the foot member and the shin member, and wherein the piston and cylinder assembly is constructed to allow the piston component to move other than axially within the cylinder component and interconnections of said piston and cylinder components to the foot and shin members are such that relative pivoting of the foot and shin members causes both axial and non-axial movement of the piston component within the cylinder component.

28. A prosthesis according to claim 27, wherein the cylinder component is associated with the shin member and the piston component has a piston and a piston rod which are pivotally connected to the foot member by a pivot joint defining a pivot axis parallel to the adjustment axis, which pivot axis is the only axis about which the piston rod is directly pivotally connected to the foot member.

29. A prosthetic ankle for a lower limb prosthesis, comprising a hydraulic mechanism that includes:
a first component and a second component adapted to be associated respectively with one and the other of a foot member and a shin member; a first direct pivot interconnecting the first and second components that defines a medial-lateral adjustment axis about which the first component and the second component are pivotable relative to each other; and a linear piston and cylinder assembly interconnecting the first and second components, the piston and cylinder assembly having a piston part translationally moveable in a cylinder part, the cylinder part having a central axis which extends substantially vertically when an amputee is standing on flat ground and which is spaced from the adjustment axis, one of said piston part and said cylinder part being rigidly connected to one of the first and second components and the other of said piston part and said cylinder part being pivotally attached to the other of the first and second components; and wherein the piston and cylinder assembly is constructed to allow the piston part to move other than axially within the cylinder part and interconnections of said piston and cylinder parts to the first and second components cause both axial and non-axial movement of the piston part within the cylinder part in response to relative pivoting of the first and second components.

30. A prosthetic ankle according to claim 29, wherein the cylinder part is adapted to be rigidly connected to a shin member and the piston part is adapted to be pivotally connected to a foot member, and wherein the piston part includes a piston and a piston rod, the piston rod being directly pivotally connected by a single pivotal connection to the said component that is associated with the foot member, the pivotal connection between the piston and said component being such that the piston pivots relative to the foot member about a pivot axis parallel to the adjustment axis.

* * * * *